United States Patent
Salisbury et al.

(10) Patent No.: US 9,345,432 B2
(45) Date of Patent: May 24, 2016

(54) SYSTEMS AND METHODS FOR SLEEP APNEA DETECTION FROM BREATHING SOUNDS

(75) Inventors: John Salisbury, Chepachet, RI (US); Ying Sun, West Warwick, RI (US)

(73) Assignee: Rhode Island Board of Education, State of Rhode Island and Providence Plantations, Providence, RI (US)

( * ) Notice: Subject to any disclaimer, the term of this patent is extended or adjusted under 35 U.S.C. 154(b) by 0 days.

(21) Appl. No.: 13/527,051

(22) Filed: Jun. 19, 2012

(65) Prior Publication Data
US 2012/0271199 A1 Oct. 25, 2012

Related U.S. Application Data

(63) Continuation of application No. PCT/US2010/062294, filed on Dec. 29, 2010.

(60) Provisional application No. 61/326,733, filed on Apr. 22, 2010, provisional application No. 61/290,602, filed on Dec. 29, 2009.

(51) Int. Cl.
*A61B 7/00* (2006.01)
*A61B 5/00* (2006.01)
*A61F 5/56* (2006.01)

(52) U.S. Cl.
CPC ............... *A61B 5/4818* (2013.01); *A61B 7/003* (2013.01); *A61B 5/7257* (2013.01); *A61F 5/56* (2013.01)

(58) Field of Classification Search
CPC ............. A61B 7/003; A61B 7/04; A61B 7/00
USPC ......................................................... 600/586
See application file for complete search history.

(56) References Cited

U.S. PATENT DOCUMENTS 5,797,852 A * 8/1998 Karakasoglu et al. ........ 600/529
6,168,568 B1 * 1/2001 Gavriely ....................... 600/529
(Continued)

FOREIGN PATENT DOCUMENTS

WO          0002486          1/2000

OTHER PUBLICATIONS

International Search Report and Written Opinion issued on Mar. 29, 2011 in connection with International Application PCT/US10/062294, 14 pages.

(Continued)

*Primary Examiner* — Sean Dougherty
*Assistant Examiner* — Daniel Cerioni
(74) *Attorney, Agent, or Firm* — Gesmer Updegrove LLP

(57) ABSTRACT

A method and an apparatus are disclosed for extending the service life of a battery source by fully utilizing the energy in batteries and/or providing higher energy reserve using multiple batteries. An universal battery bank consists of an ensemble of possibly heterogenous batteries all connected in series to provide a usable operational energy source. For a universal battery bank consists on N batteries, the minimum operational voltage for the individual batteries (Vmin) can be lowered to Vmin/N on average, thereby extending the time interval between battery replacements and draining the individual batteries more efficiently. To exploit this power supply that may vary over a wide voltage range, electronics are designed to monitor the individual batteries, guard against excessive voltage and current, and provide constant current sources and/or constant voltage sources for various appliances.

13 Claims, 8 Drawing Sheets

(56) References Cited

U.S. PATENT DOCUMENTS

| | | | |
|---|---|---|---|
| 6,213,955 | B1 | 4/2001 | Karakasoglu et al. |
| 6,261,238 | B1* | 7/2001 | Gavriely .................. 600/532 |
| 6,942,626 | B2* | 9/2005 | Salisbury et al. .......... 600/538 |
| 2006/0155205 | A1* | 7/2006 | Sotos et al. ............... 600/529 |
| 2006/0198533 | A1* | 9/2006 | Wang et al. ................. 381/67 |
| 2007/0173730 | A1* | 7/2007 | Bikko ........................ 600/538 |
| 2008/0275349 | A1* | 11/2008 | Halperin et al. ........... 600/484 |
| 2012/0004749 | A1* | 1/2012 | Abeyratne et al. ........... 700/94 |

OTHER PUBLICATIONS

International Preliminary Report on Patentability issued on Jul. 12, 2012 in connection with International Application PCT/US2010/062294, 8 pages.

Basano et al., "A DSP Breath Sound Analyzer," University of Genova, Jun. 7, 1988, pp. 2631-2634.

Bassingthwaighte et al., "Fractal Correlation in Heterogeneous Systems," Physica D: Nonlinear Phenomena v. 53, No. 1, 1991, pp. 71-84.

Buyalo et al., "Asymptotic Dimension of a Hyperbolic Space and Capacity Dimension of its Boundary at Infinity," St. Petersburg Math Journal, vol. 17, No. 2, 2006, pp. 267-283.

Collop et al., "Clinical Guidelines for the Use of Unattended Portable Monitors in the Diagnosis of Obstructive Sleep Apnea in Adult Patients," The Journal of Clinical Sleep Medicine, vol. 3, No. 7, 2007, pp. 737-747.

Cooley et al., "The Fast Fourier Transform and its Applications," IEEE Transactions on Education, vol. 12, No. 1, Mar. 1969, pp. 37-34.

Gay et al., "Are Sleep Studies Appropriately Done in the Home?" Respiratory Care, vol. 55, No. 1, Jan. 2010, pp. 66-75.

Huang, et al., "The Empirical Mode Decomposition and the Hilbert Spectrum for Non-Linear and Non-Stationary Time Series Analysis," Proceedings of the Royal Society of London, Series A, No. 454, 1998, pp. 903-995.

Hwang et al., Information Dimension, Information Overload and Decision Quality, Journal of Information Science, vol. 25, No. 3, 1999, pp. 213-218.

Nieto et al., "Association of Sleep-Disordered Breathing, Sleep Apnea, and Hypertension in a Large Community-Based Study," Journal of the American Medical Associate, vol. 284, No. 14, Apr. 2000, pp. 1829-1836.

Pasterkamp et al., "Posture-Dependent Change of Tracheal Sounds at Standardized Flows in Patients with Obstructive Sleep Apnea," American College of Chest Physicals, vol. 110, No. 6, Dec. 1996, pp. 1493-1498.

Salisbury et al., "Rapid Screening Test for Sleep Apnea Using a Nonlinear and Nonstationary Signal Processing Technique," Medical Engineering & Physics, vol. 29, 2007, pp. 336-343.

Australian Office Action issued on May 17, 2013 for Australian Patent Appln. No. 2010339554 filed on Feb. 4, 2013, 3 pages.

Examination Report issued on Jul. 30, 2015 by the European Patent Office in connection with related European Patent Application No. 10798702.6, 4 pages.

Communication pursuant to Rules 161(1) and 162 EPC issued on Sep. 7, 2012 by the European Patent Office in connection with related European Patent Application No. 10798702.6, 2 pages.

* cited by examiner

SYSTEMS AND METHODS FOR SLEEP APNEA DETECTION FROM BREATHING SOUNDS

PRIORITY INFORMATION

The present application is a continuation of International Patent Application No. PCT/US10/62294 filed on Dec. 29, 2010, which claims priority to U.S. Provisional Patent Applications Nos. 61/326,733 filed Apr. 22, 2010 and 61/290,602 filed Dec. 29, 2009, the entire disclosures of each of which are hereby incorporated by reference.

BACKGROUND

The present invention generally relates to the medical condition of obstructive sleep apnea, and relates in particular to systems and methods for detecting obstructive sleep apnea in the awake state.

Obstructive sleep apnea (OSA) is caused by the collapse of the tongue and soft palate onto the posterior pharyngeal wall, which obstructs the airway intermittently during sleep. Loud snoring, in combination with obesity, is known to be highly predictive of OSA. Symptoms of OSA are known to include pauses or reduction in breathing during sleep, having an unrefreshed feeling after sleep, and excessive daytime sleepiness. OSA has been reported to be associated with serious health consequences due to the increasing risk of cardiovascular disease, stroke, hypertension, arrhythmias, diabetes, and sleep deprived driving accidents. The prevalence of sleep apnea is reported to be not well defined due to an expected high level of under diagnosis; it has been estimated that about 20% of the adults in the United States have OSA, of whom only about 10% have been diagnosed.

The conventional diagnosis of OSA relies on testing done during an overnight sleep study using polysomnography. A value referred to as the apnea hypopnea index (AHI) is the average number of apneas and hypopneas per hour of sleep determined from the polysomnographic study. The AHI index values have been used to classify OSA as mild (AHI=5-15), moderate (AHI=15-30), and severe (AHI>30). While apnea is defined as the cessation of airflow for more than 10 seconds, the definition of hypopnea is yet to be standardized. In addition to the original (Chicago) definition of hypopnea that requires either >50% airflow reduction or a lesser airflow reduction with associated >3% oxygen desaturation or arousal, two other stricter definitions have been used by others. The overnight polysomnographic study is highly specialized, expensive and time consuming, which has contributed in part to the under diagnosis of OSA.

Several simplified portable devices have been developed to facilitate unattended home-based sleep studies for the diagnosis of OSA. These devices may typically be used at the individual's own home, thereby obviating inconvenience and the high cost of using a sleep laboratory study. A guideline established by the Portable Monitoring Task Force of the American Academy of Sleep Medicine suggests that such devices can be used in patients with a high pretest probability of moderate to severe OSA, but are not appropriate for general screening of asymptomatic populations (see *Clinical guidelines for the use of unattended portable monitors in the diagnosis of obstructive sleep apnea in adult patients*, by N. A. Collop, W. M. Anderson, B. Boehlecke, D. Claman, R. Goldberg, D. J. Gottlieb, D. Hudgel, M. Sateia and R. Schwab, J. Clinical Medicine, v. 3, no. 7, pp. 737-747 (2007)). A 2010 review of the effectiveness of home-based sleep studies concludes that more outcome-oriented studies are needed to resolve the controversy surrounding the appropriateness of home-based sleep studies (see *Are sleep studies appropriately done in the home?*, by P. D. Gay and P. A. Selecky, Respiratory Care, v. 55, no. 1, pp. 66-75 (2010)).

The article *Rapid screening test for sleep apnea using a non-linear and non-stationary signal processing technique*, by J. Salisbury and Y. Sun (the present inventors), Medical Engineering and Physics, v. 29, no. 2, pp. 150-157 (2007), discloses a method to detect OSA from a 5-minute daytime recording of the nasal airway pressure. Due to the non-linear and non-stationary nature of the signal, the Hilbert-Huang transform (see *The empirical mode decomposition and the Hilbert spectrum for non-linear and non-stationaty time series analysis*, by N. E. Huang, Z. Shen, S. R. Long, M. C. Chu, H. H. Shih and A. Zheng, Proceedings of the Royal Society of London, Series A, no. 454, pp. 903-995 (1998)) was used to extract signals intrinsic to OSA. The Hilbert spectrum was centered around 1.5 Hz for normal subjects and shifted upward in frequency scale with increased likelihood of OSA. Although this study did find that it was possible to obtain a marker for OSA from data collected in the waking state, the methodology has not been fully successful in accurately identifying OSA conditions in all subjects and requires extensive computation.

The article *Posture-Dependent Change of Tracheal Sounds at Standardized Flows in Patients With Obstructive Sleep Apnea*, by H. Pasterkamp, J. Schafer and G. Wodicka, American College of Chest Physicians, v. 110, no. 6, pp. 1493-1498 (1996), discloses performing measurements of the tracheal sound intensity (TSI) from a subject in order to detect increased sound levels when a patient is in a supine position, thereby indicating increased flow resistance in the trachea. The analysis of the data involved determining an average power spectrum of tracheal sounds within low (0.2 to 1 KHz), medium (1 to 2 KHz), and high (2 to 3 KHz) frequency bands for each subject. The study found that at the same inspiratory flow, the increase in tracheal sound intensity from upright to supine position was greater in OSA patients than in control subjects. The control subjects, however, were significantly younger, not obese and did not include snorers. There remains a need, therefore, for an efficient and effective sleep apnea test system and method that may readily detect sleep apnea for a subject in a waking state during daytime in the office of a primary-care physician.

SUMMARY

In accordance with an embodiment, the invention provides a method of detecting obstructive sleep apnea in subject. The method includes the steps of placing a head of an electronic stethoscope at the subject's suprasternal notch, providing an electrical signal representative of the sounds detected by the head of the electronic stethoscope within a frequency range, determining an obstructive sleep apnea index based on a ratio of the amount of the electrical signal that is associated with a frequency below a cut-off frequency with respect to a total amount of energy associated with the entire frequency range, and identifying the subject as having obstructive sleep apnea if the obstructive sleep apnea index is above a window maximum or below a window minimum.

In accordance with another embodiment, the invention provides a method of detecting obstructive sleep apnea in subject that includes the steps of placing a head of an electronic stethoscope at the subject's suprasternal notch, providing an analog electrical signal representative of the sounds detected by the head of the electronic stethoscope within a frequency range, receiving the analog electrical signal and providing a digitized electrical signal that is representative of the analog electrical signal with the frequency range, applying a fast Fourier transform to the digitized electrical signal, determining an obstructive sleep apnea index based on a ratio of the amount of the electrical signal that is associated with a frequency below a cut-off frequency with respect to a total amount of energy associated with the entire frequency range, identifying the subject as having obstructive sleep apnea if the obstructive sleep apnea index is above a window maximum or below a window minimum, and identifying the subject as not having obstructive sleep apnea if the obstructive sleep apnea index is within a window defined by the window maximum and the window minimum.

In accordance with a further embodiment, the invention provides a system for detecting obstructive sleep apnea in subject. The system includes an electronic stethoscope having a head for application to a subject, a processor and a display. The processor is for determining an obstructive sleep apnea index based on a ratio of the amount of the electrical signal that is associated with a frequency below a cut-off frequency with respect to a total amount of energy associated with the entire frequency range, and for determining whether the obstructive sleep apnea index is above a window maximum or below a window minimum. The display is for providing an identification of whether the subject has obstructive sleep apnea responsive to whether the obstructive sleep apnea index is above the window maximum or below the window minimum.

BRIEF DESCRIPTION OF THE DRAWINGS

The following description may be further understood with reference to the accompanying drawings in which.

The drawings are shown for illustrative purposes only.

DETAILED DESCRIPTION

The invention involves identifying that the soft tissues and anatomical structures causing OSA in the sleeping state also contribute to detectable changes of breathing sounds recorded in the waking state coming from the area of the subject's suprasternal notch, which is between the subject's sternocleidomastoid muscles, and inferior to the subject's larynx (the large visible dip bordered by the subject's clavicle notches and the manubrium of the sternum). The analysis involved a prospective human study to collect breathing sounds from normal and OSA subjects, and the identification of an appropriate OSA marker from the breathing sounds by applying various linear and nonlinear signal analysis techniques.

Figure 1:
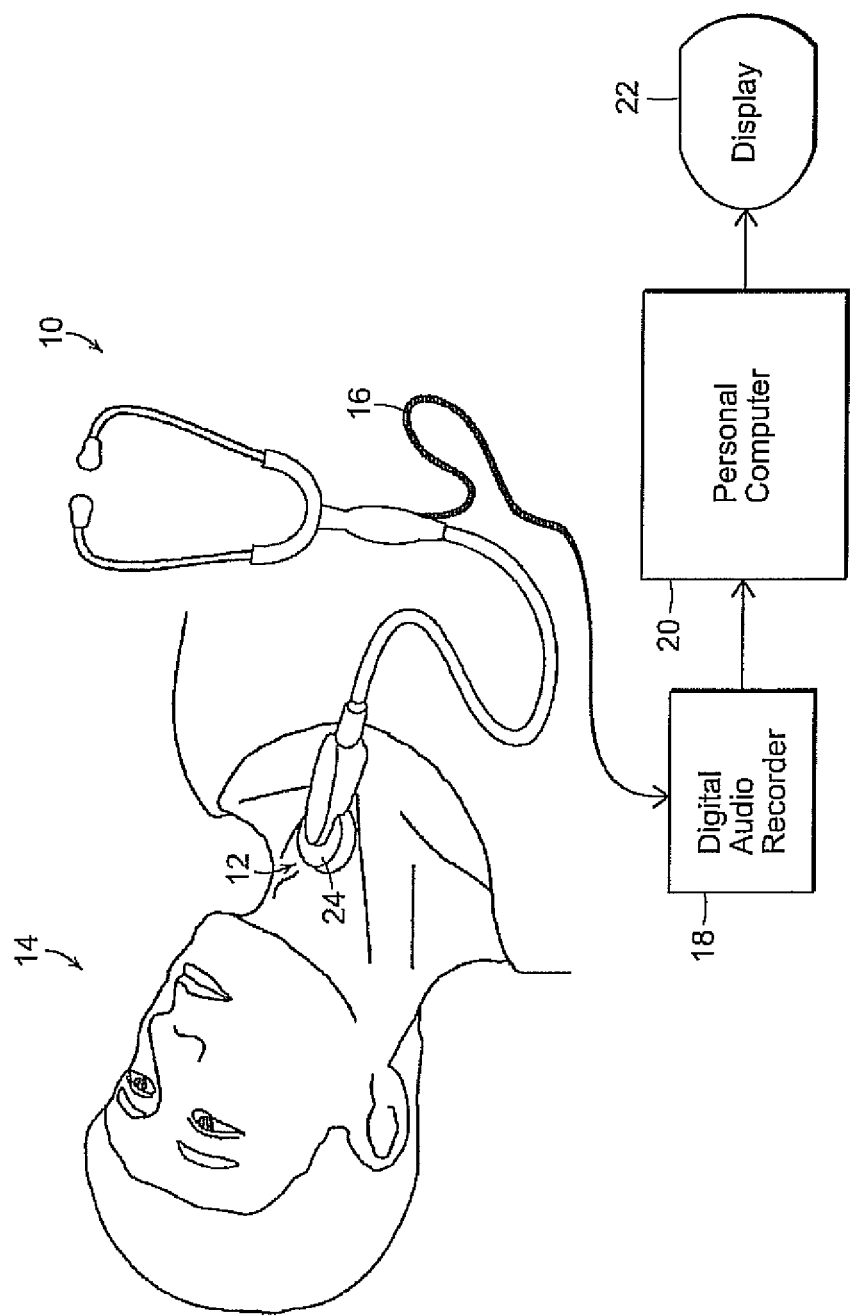
FIG. 1 shows an illustrative diagrammatic view of an OSA detection system for use in accordance with an embodiment of the present invention.

As shown in FIG. 1, an electronic stethoscope 10 was used to record breathing sounds from the suprasternal notch 12 with the subject 14 lying in a flat-supine position. The electronic stethoscope 10 (such as a JABES stethoscope sold by GSTechnology of Seoul, Korea) includes an internal microphone and outputs an analog electrical signal. The analog electrical signals were provided (via cable 16) to a digital to analog converter within a digital audio recorder 18, which was in communication with a personal computer 20 that included an output display 22. In other embodiments, the data may be transferred to a processing system through a variety of known techniques, such as wireless transfer, the use of universal serial bus (USB) data storage devices, or other personal data devices.

The frequency range of the electronic stethoscope 10 was set to the wide mode, between 20 Hz and 800 Hz, which includes both the low frequency range from the bell and the high frequency range from the diaphragm of a conventional stethoscope. The digital audio recorder 18 was, for example, a Zoom H4 hand-held digital audio recorder (sold by Zoom Corporation of Tokyo, Japan). The recording mode was set at the WAV format with 44.1 KHz sampling and 16-bit quantization.

As shown in FIG. 1, with the subject lying in a flat supine position, the stethoscope head 24 was placed over the subject's suprasternal notch 12, between the subject's sternocleidomastoid muscles, and inferior to the subject's larynx. The subject 14 was asked to relax and take 6-8 deep breaths through the mouth during the data acquisition. The acquisition time was about 15 seconds, depending on the subject's respiratory rate. The acoustic data was stored on a memory card in the hand-held recorder and uploaded to a personal computer via a USB port for subsequent analyses.

Data was collected from 7 normal subjects (AHI<5) and 11 OSA subjects (AHI≥5). To identify a suitable marker for OSA several parameters were systematically studied. While nonlinear parameters such as fractal correlation and information dimension were indicative, a simple and reliable marker came from the frequency spectrum. For normal subjects, the frequency spectrum showed a prominent peak at 40 Hz with a secondary peak at 500 Hz. For OSA subjects, the frequency spectrum changed in two distinct ways, either shifting the prominence to the 500 Hz peak or concentrating all energy in the 40 Hz peak with almost no higher-frequency components. Based on this observation the OSA Index was defined as the percent signal energy below 100 Hz in the frequency spectrum. If the OSA Index was either below 25% or above 80%, the subject was considered at risk of OSA. The detection algorithm yielded one false positive and no false negative, showing 100% sensitivity and 86% specificity. This study characterized OSA-related changes in frequency spectra of breathing sounds and demonstrated the feasibility of a screening test for OSA during routine checkups at a physician's office. Such a screening device could be easily incorporated into the design of a standard stethoscope.

The data analysis was done on the personal computer 20 using the Matlab Signal Processing Toolbox program (sold by Mathworks, Inc. of Natick, Mass.). The digitized breathing signals were first decimated by a factor of 8, resulting in a sampling rate of 5,512.5 Hz. The data set consisted of 18 data segments, again, 7 from normal subjects and 11 from OSA subjects. Initially, during the search for an OSA marker, the empirical mode decomposition was used to decompose each data segment into an ensemble of intrinsic mode functions (IMFs). The subsequent data analyses were applied to the original data segment, a specific IMF, or a combination of selected IMFs.

In order to identify an appropriate marker for differentiating OSA subjects from normal subjects, the data set was systematically processed with a variety of linear and nonlinear signal analysis techniques. The use of fast Fourier transform (FFT) analyses was employed to analyze the data (see *The fast Fourier transform and its applications*, by J. W. Cooley, P. A. W. Lewis, and P. D. Welch. IEEE Trans Education 12(1):27-34, 1969).

A variety of other techniques may be employed in other embodiments for analyzing the data in certain applications, including for example, fractal correlation techniques (see *Fractal correlation in heterogeneous systems*, by J. Bassingthwaighte and R. Bever, Physica D: Nonlinear Phenomena v. 53, no. 1, pp. 71-84, 1991), capacity dimension techniques (see *Asymptotic dimension of a hyperbolic space and capacity dimension of its boundary at infinity*, by S. Buyalo, St. Petersburg Math J v. 17, pp. 267-283, 2006), and information dimension techniques (see *Information dimension, information overload and decision quality*, by M. I. Hwang and J. W. Lin, Journal of Information Science, v. 25, pp. 213-218, 1999). Parameters based on the aforementioned techniques may be extracted from the data segments and/or their IMFs. Each parameter may be examined for its ability to separate the OSA subjects from the normal subjects for certain applications.

Figure 2:
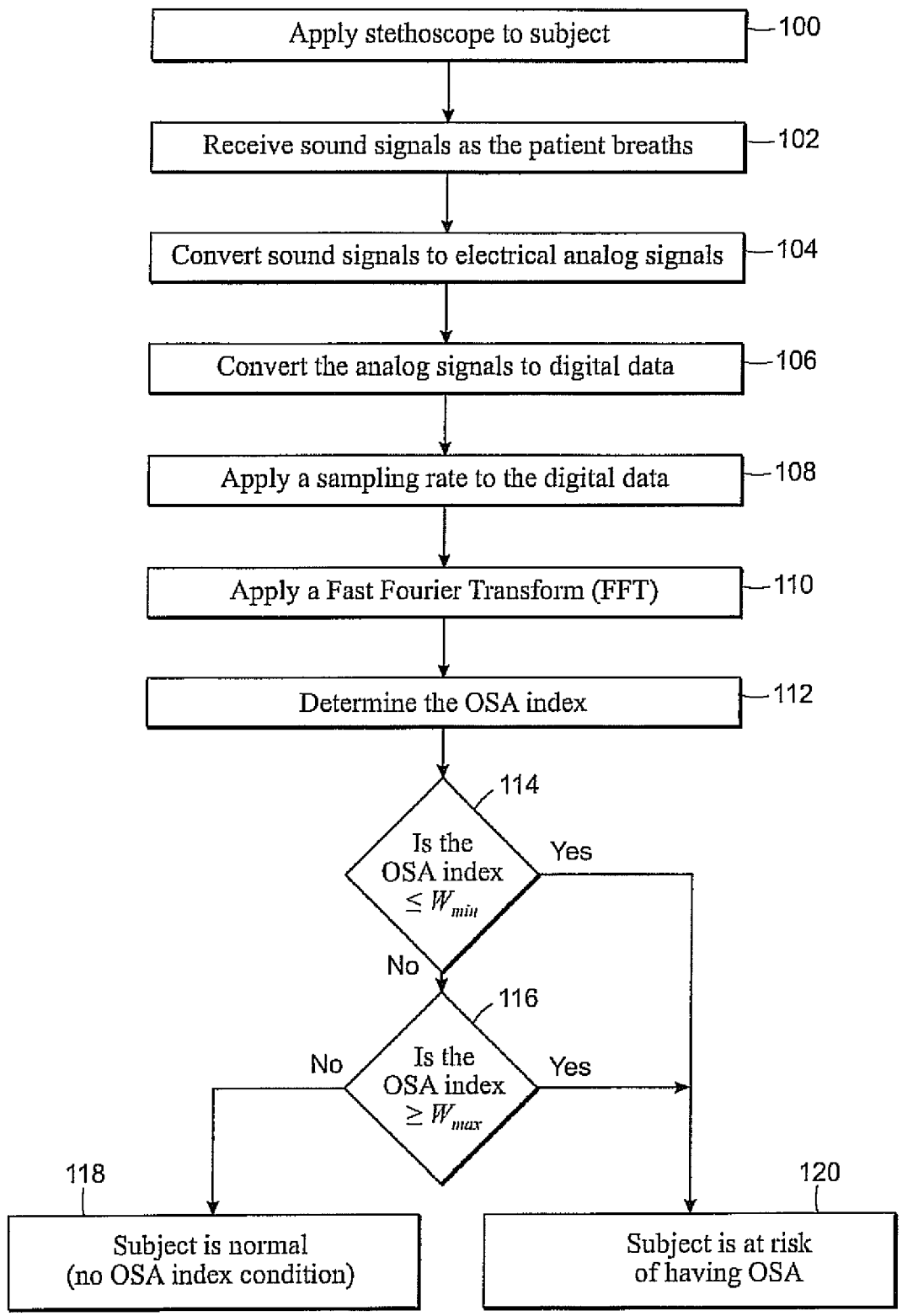
FIG. 2 shows an illustrative flowchart of a process of OSA detection in accordance with an embodiment of the present invention.

FIG. 2 shows an illustrative flowchart of a process of OSA detection in accordance with an embodiment of the present invention. The process begins (step 100) with a caregiver positioning the stethoscope head 24 over the subject's suprasternal notch 12 (as shown in FIG. 1). The sounds from the subject breathing are then received (step 102), and are converted to analog electrical signals by the stethoscope 10 (step 104). The analog electrical signals are provided to the digital audio recorder 18 where they were digitized (step 106), and a sampling rate was applied to the digitized data (step 108). The digital audio recorder then provided to the personal computer 20 where a fast Fourier transform (HT) analysis was performed to provide frequency domain data (step 110). The frequency domain data was then analyzed to provide an OSA index (step 112). If the OSA index was less than or equal to a window minimum ($W_{min}$) of for example, 25% (step 114), the system would indicate that the subject was at risk of having OSA (step 120). If the OSA index was greater than or equal to a window maximum ($W_{max}$) of for example, 80% (step 116), the system would indicate that the subject was also at risk of having OSA (step 120). For example, therefore, if the OSA index was greater than 25% (step 114) but less than 80% (step 116), then the system would indicate that the person appears to not have an OSA condition (step 118) in accordance with an embodiment of the invention. An indication of whether the subject has an OSA condition is provided on the display 22 of FIG. 1.

Table 1 below summarizes the demographic data, body mass index (BMI) and apnea-hypopnea indexes (AHI) for the control group (7 normal subjects) and the experimental group (11 OSA subjects). A 2-tailed unpaired t-test showed that there was no significant difference in age between the two groups (P=0.36). There was a significant difference in the body mass index (BMT) between the two groups (P<0.05).

TABLE 1

|  | Age | Sex | BMI | AHI |
|---|---|---|---|---|
| Normal (n = 7) | 55 ± 18 (38-91) | 4M, 3F | 25.5 ± 3.4 | <5 or asymptomatic |
| OSA (n = 11) | 63 ± 14 (43-84) | 9M, 2F | 31.3 ± 6.4 | 23 ± 16 (9-54) |

Fractal correlation, capacity dimension, information dimension, and FFT, were found to be effective for detecting OSA. Fractal correlation, capacity dimension, and information dimension were indicative of OSA only when they were extracted from selected sections of the data segments; they failed to provide accurate detection of OSA when data segments in their entirety were used. The most reliable and accuracy marker came from the frequency spectrum, which was obtained by applying FFT to the entire original data segment. It was not necessary to use the empirical mode decomposition to extract EIVIFs from the original data segment.

Figure shows the steps taken to determine the OSA index (step 112 in FIG. 2). First, the total energy of the recorded signal over a wide range of ($f_{min}$, to $f_{max}$), for example 20 Hz to 800 Hz (or 0 Hz to 800 Hz), is determined (step 200) as $$\sum_{f_{min}-f_{max}} X^2(w)$$

(step 200). Then the amount of energy of the measured signal below a cut-off frequency ($f_{cut}$) of, for example, 100 Hz, is determined (step 202) as $$\sum_{f_{min}-f_{cut}} X^2(w).$$

Then the following ratio is determined and multiplied by 100 (step 204)

$$\frac{\sum_{f_{min}-f_{cut}} X^2(w)}{\sum_{f_{min}-f_{max}} X^2(w)}.$$

The process then returns (step 206) to the method in FIG. 2 at step 114.

The frequency spectrum of the breathing sound X (w), where w=2πf, was computed by averaging the FFT's from consecutive time windows over the relevant data segment (typically about 15 s). The size of the FFT window was chosen to be 1024 samples (or 186 ms), resulting in a frequency resolution of 2.69 Hz. The OSA Index was therefore, defined as the percent signal energy below 100 Hz on the frequency spectrum of the breathing signals. For the above specific example, therefore:

$$\text{OSA Index (\%)} = \sum_{0-100\,KHz} X^2(w) \Big/ \sum_{0-800\,KHz} X^2(w) \times 100$$

Two thresholds were therefore used to detect OSA according to the following: If 25%<OSA Index<80%, then the subject does not have an OSA condition. If the OSA Index≤25% or the OSA Index≥80%, then the subject is at risk of having an OSA condition. The sensitivity of the FFT window size was tested by setting it to either 512 or 2048. In each case the resulting OSA Index was exactly the same as that obtained with the 1024 window.

Figure 4:
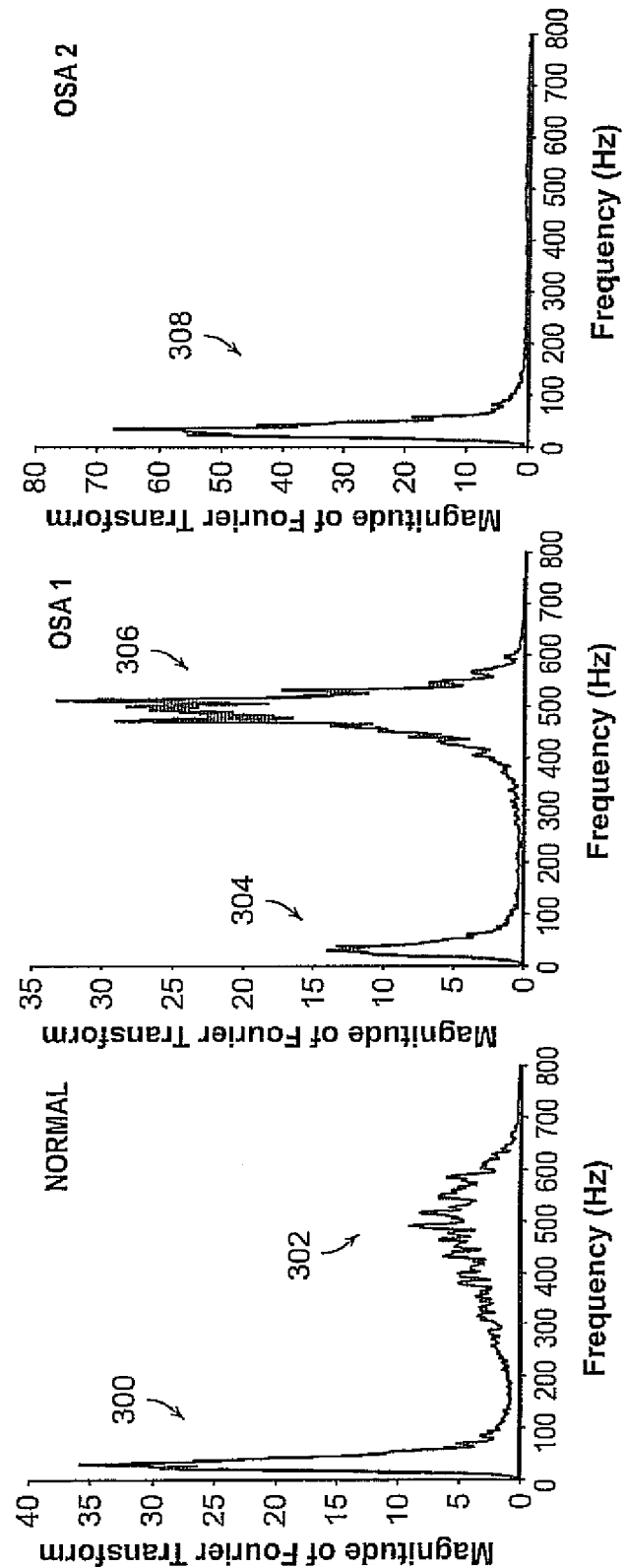
FIGS. 4A-4C show illustrative graphical views of frequency spectrums of breathing sounds for a normal subject and two OSA subjects respectfully.

The identification of the OSA marker was based on an observation of the characteristic patterns of the frequency spectra of breathing sounds associated with the normal and OSA subjects. As shown in FIG. 4A, the typical frequency spectrum from normal subjects had a prominent peak below 100 Hz (as shown at 300), usually centered about 40 Hz. A less prominent peak appeared (as shown at 302) in the higher-frequency range, usually centered about 500 Hz. For OSA subjects, the frequency spectrum changed into two distinctly different patterns. As shown in FIG. 413, the first OSA pattern showed an up-shift of the frequency components, making the 500 Hz peak the prominent one (as shown at 306), while the peak between 0 and 100 Hz was reduced (as shown at 304). As shown in FIG. 4C, the second OSA pattern changed in a totally opposite way. Almost all signal energy was concentrated in the 40 Hz peak (as shown at 308), typically between 10 and 70 Hz, with very little or no frequency components above 100 Hz.

Figure 5:
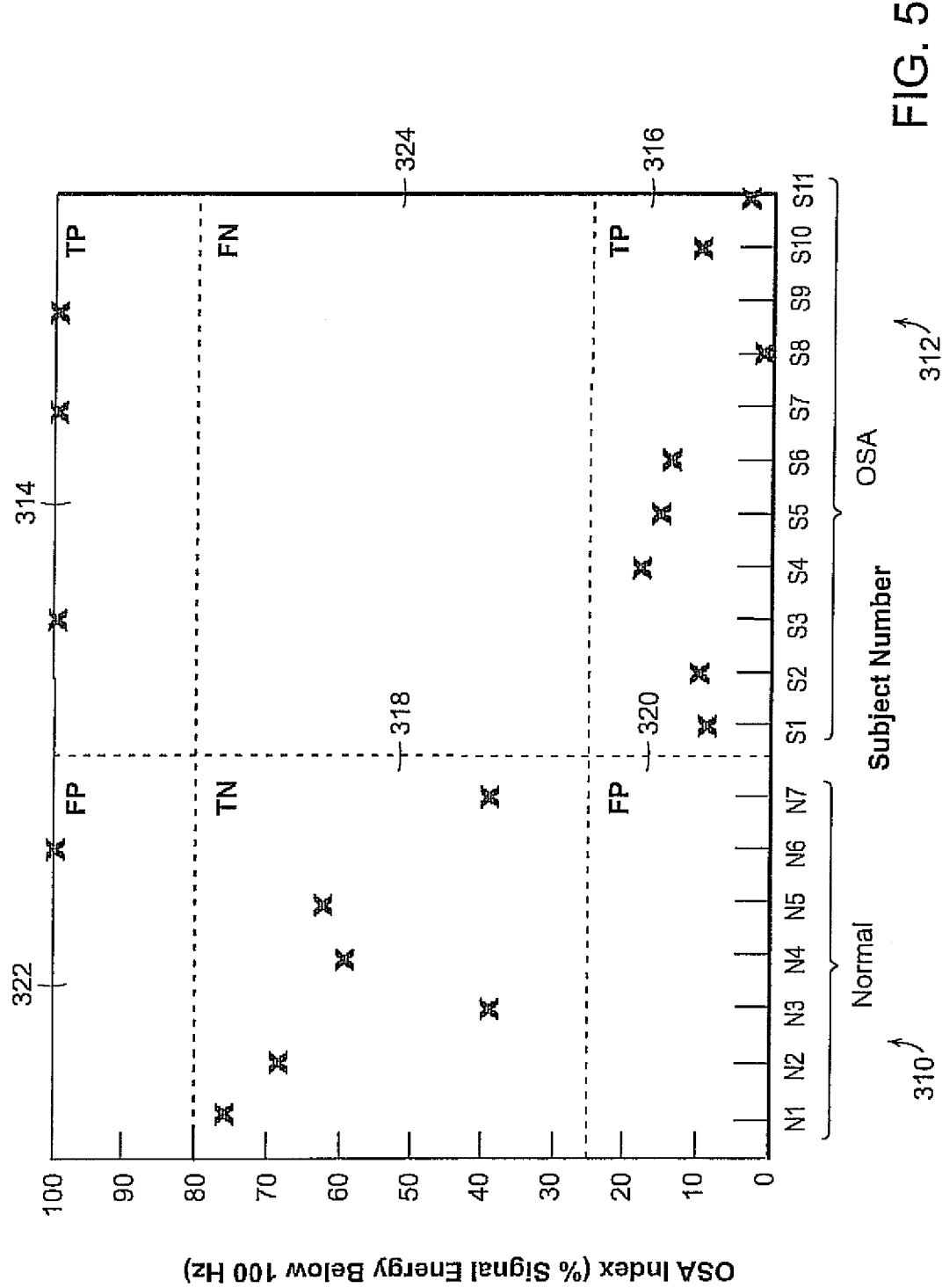
FIG. 5 shows an illustrative graphical view of OSA index values for seven normal subjects and eleven OSA subjects.

As shown in FIG. 5, the OSA Index was computed for the 7 normal subjects (N1 to N7) as shown at 310, and 11 OSA subjects (S1 to S11) as shown at 312. Two thresholds at 25% and 80%, respectively, were used to define the detection zones for true positive (TP) shown at 314 and 316, true negative (TN) shown at 318, false positive (FP) shown at 320 and 322, and false negative (FN) shown at 324. This detection algorithm yielded one FP (subject N6) and no FN, showing 100% sensitivity and 86% specificity.

In accordance with an embodiment, therefore, the invention identifies that the soft tissues causing obstructive sleep apnea also contribute to detectable changes of breathing sounds recorded in the waking state. The frequency up-shift may be related to the fundamental frequency with associated harmonics of the soft palate vibration, which are typically under 500 Hz. The reason for the frequency down-shift may be related to the reduction of high frequencies of obstructed snoring in hypopnea-dominated subjects. The frequency spectrum of the detected sounds has been found to provide a robust, repeatable and accurate marker for detecting OSA in accordance with invention. In an embodiment, the OSA Index was defined as the percent signal energy below 100 Hz in the frequency spectrum of the breathing sound. An OSA Index either below 25% or above 80% was considered a risk factor; the resulting detection algorithm showed 100% sensitivity and 86% specificity. The invention provides that it is feasible to accurately detect OSA based on breathing signals recorded in the waking state.

Although the above study was based on a small data set (7 normal and 11 OSA subjects), the subjects' demographic data was very consistent with that reported in the literature. The BMI was 25.5±3.4 for the control group and 31.3±6.4 for the OSA group, comparable to 27.0 and 30.2, respectively, found in the Sleep Heart Health Study on 6132 subjects as reported in *Association of Sleep-Disordered Breathing, Sleep Apnea, and Hypertension in a Large Community-Based Study*, by F. J. Nieto, T. B. Young, B. K. Lind, E. Shahar, J. M. Samet, S. Redline, R. B. DrAgostino, A. B. Newman, M. D. Lebowitz, and T. G. Pickering, Journal of the American Medical Association, no. 283, pp. 1829-1836 (2000). In certain reports, BMI has been suggested as a predictor for OSA, yet in the above study using BMI>28 to detect OSA, resulted in a relatively weak predictor with 64% sensitivity and 71% specificity.

Because snoring is indicative of OSA, several previous studies were devoted to the analysis of snoring sounds recorded with a stethoscope, or the analysis of breathing sounds of a patient standing versus lying down. Advantages of the present approach include that the required duration of recording is relative short, about 15 s depending on the subject's respiratory rate, and that the procedure is performed by a medical expert, thereby avoiding the concern of lacking supervision as raised for home-based sleep studies with portable monitoring devices.

Figure 3:
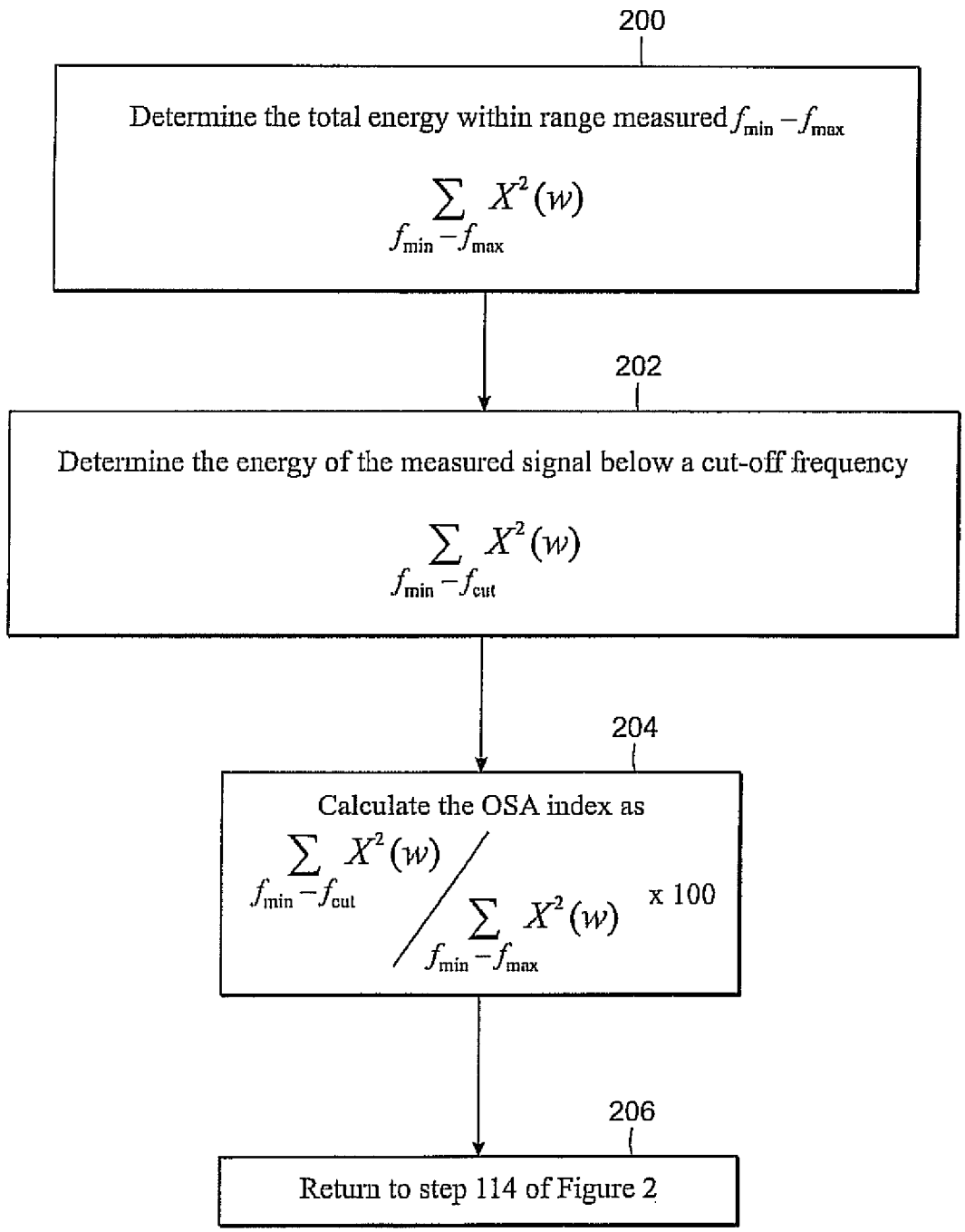
FIG. 3 shows an illustrative flowchart of a process for the OSA index determination step of FIG. 2 in accordance with an embodiment of the present invention.
Figure 6:
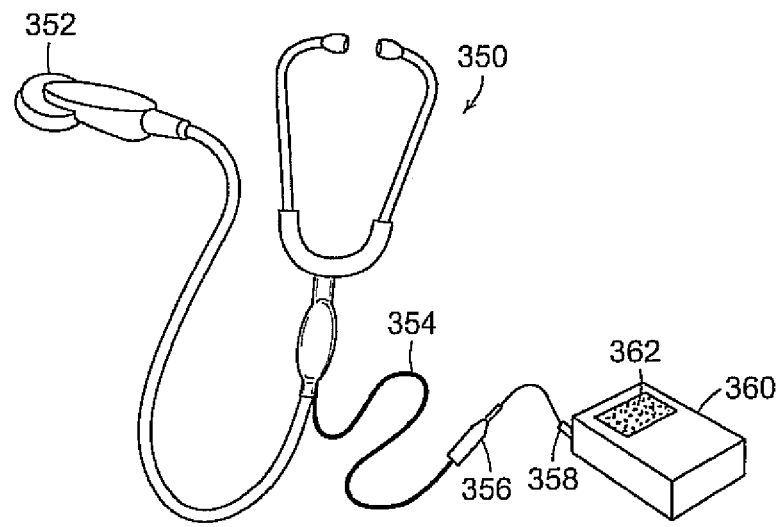
FIG. 6 shows an illustrative diagrammatic view of an OSA detection system for use in accordance with another embodiment of the present invention.

FIG. 6, for example, shows an OSA detection system in accordance with another embodiment of the invention that is similar to that shown in FIG. 1 but includes the digital audio recorder, personal computer and display functionality in one specialized device. In particular, an electronic stethoscope 350 has a head 352 for application to a subject's suprasternal notch as discussed above. The electronic stethoscope 350 includes an output cable 354 having a coupling adaptor 356 for attaching to a port 358 of an OSA detection unit 360. The OSA detection unit 360 includes a processor that specially is programmed to carry out the steps discussed above with reference to FIGS. 2 and 3. An indication of whether the subject has an OSA condition is provided on the display 362. The system may therefore be provided in a convenient, portable kit.

Figure 7:
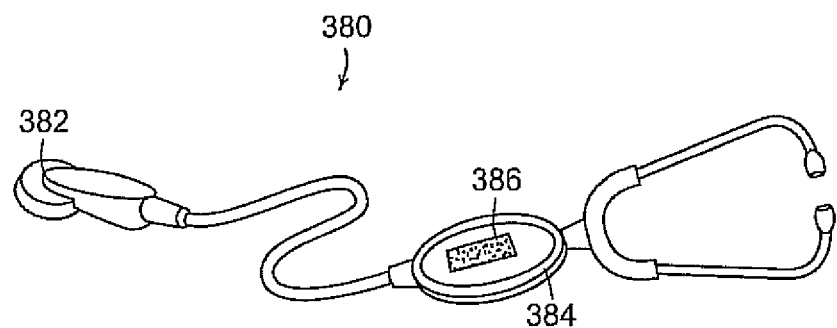
FIG. 7 shows an illustrative diagrammatic view of an OSA detection system for use in accordance with a further embodiment of the present invention.

FIG. 7 shows an example of an OSA detection system in accordance with a further embodiment of the invention that is also similar to that shown in FIG. 1 but includes the digital audio recorder, personal computer and display functionality in the stethoscope itself. In particular, an electronic stethoscope 380 has a head 382 for application to a subject's suprasternal notch as discussed above. The electronic stethoscope 380 includes an internal OSA detection unit 384 that specially is programmed to carry out the steps discussed above with reference to FIGS. 2 and 3. An indication of whether the subject has an OSA condition is provided on the display 386. The system may therefore be provided in a convenient, unitary electronic stethoscope specially designed for detecting OSA condition.

The present invention differs from the method disclosed in *The empirical mode decomposition and the Hilbert spectrum for non-linear and non-stationary time series analysis*, by N. E. Huang, Z. Shen, S. R. Long, M. C. Chu, H. H. Shih and A. Zheng, Proceedings of the Royal Society of London, Series A, no. 454, pp. 903-995 (1998) at least in that the acoustic signal of the breathing sound is used instead of the nasal airway pressure. The higher frequency range of the acoustic signals has the advantages of reducing the data acquisition time significantly and permitting the collection of data via a stethoscope—a standard instrument familiar to all physicians. In addition, the resulting signal processing technique is entirely different and much simpler, allowing for the integration of the OSA detection system into an electronic stethoscope using an inexpensive embedded processor, as discussed above.

The present invention is significantly different from the aforementioned methodology employed by Pasterkamp et al. (*Posture-Dependent Change of Tracheal Sounds at Standard-*

*ized Flows in Patients With Obstructive Sleep Apnea*, by H. Pasterkamp, J. Schafer and G. Wodicka, American College of Chest Physicians, v. 110, no. 6, pp. 1493-1498 (1996)) in at least the following aspects.

1. Difference in instrumentation: Pasterkamp et al. used a piezoelectric accelerometer attached with double-sided adhesive tape over the trachea in the midline between cricoid and suprasternal notch, whereas the present invention employs a standard stethoscope positioned right at the supersternal notch.
2. Difference in the acoustic frequency range: Pasterkamp et al. employed a low-pass filter with a cut-off frequency at 50 Hz, whereas the present invention includes the low frequencies from 20 Hz and up. This difference is significant I that it has a profound consequence as the study showed that a peak around 40 Hz in the frequency spectrum of the breathing sound provides an important characteristic in detecting OSA.
3. Difference in the detection approach: Pasterkamp et al. used the absolute sound level (i.e. TSI) as a marker for OSA, whereas the present invention uses the relative distribution of low (around 40 Hz) vs. high (around 500 Hz) frequencies as a marker for OSA. Thus, the use of the relative spectral distribution has the advantage of higher reliability and avoiding the need for calibrating the absolute level of the recorded sound.
4. The present invention is based on a new finding of two drastically different ways of spectral changes in OSA subjects, which was not reported by Pasterkamp et al. or any other researchers. One group of OSA subjects showed an up-shift of acoustic energy to the 500 Hz peak, while the other group of OSA patients showed an down-shift of acoustic energy with essentially no signals above 100 Hz. This new clinical finding provides the basis of the present invention and results in a simple but accurate way of detecting OSA with the subjects in the awake state.

Figure 8:
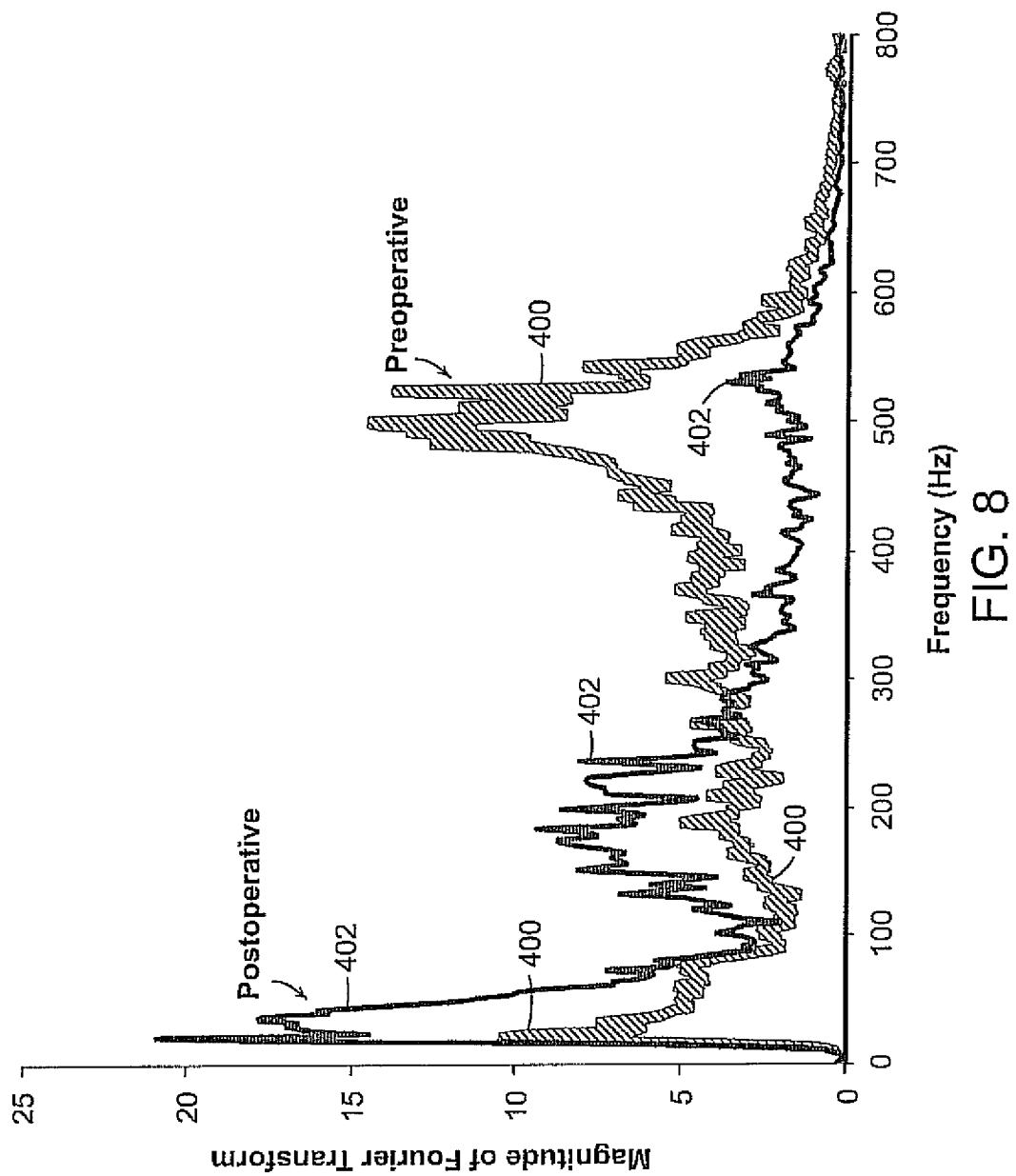
FIG. 8 shows an illustrative graphical view of a frequency spectra of a subject preoperative and after having undergone palatouvuloplasty.

One of the subjects in the above study had OSA, which was later successfully treated with a surgical procedure to remove parts of the palate and/or the uvula. The surgical procedure is called palatouvuloplasty. The availability of both preoperative (S5) and postoperative (N5) recordings from this subject provided a unique opportunity to investigate the effects of palatouvuloplasty on breathing sounds. FIG. 8, for example, shows the preoperative spectrum (shown at 400) overlapped with the postoperative spectrum (shown at 402) for comparison. The prominent peak at 500 Hz of the preoperative spectrum was significantly suppressed after the surgery. The postoperative spectrum showed a prominent peak around 40 Hz and a secondary peak around 200 Hz.

Figure 9:
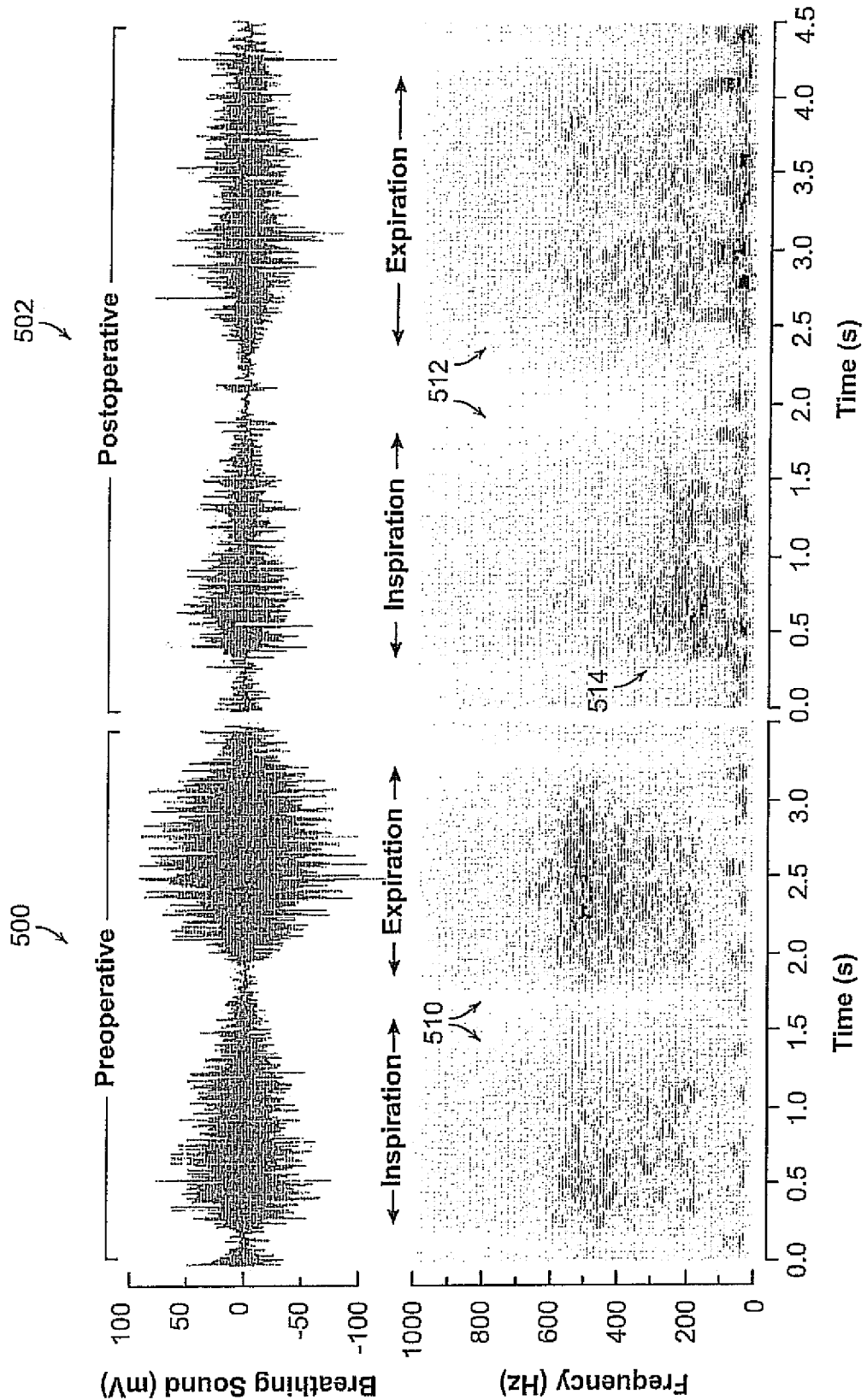
FIG. 9 shows an illustrative graphical view of both preoperative and postoperative breathing sounds and spectrograms of a palatouvuloplasty subject.

To probe further about when these frequency components occur during the respiratory cycle, the spectrograms were computed by use of the short-time Fourier transform. FIG. 9 shows the preoperative (shown at 500) and postoperative (shown at 502) breathing sounds were shown for a respiratory cycle with an inspiration followed by an expiration. FIG. 9 also shows (at 510 and 512 respectively) plots of the corresponding spectrograms. The preoperative spectrogram (shown at 510) showed intense activities around 500 Hz during expiration, which disappeared in the postoperative spectrogram (shown at 512). The postoperative spectrogram showed some activities spread around 200 Hz during inspiration (as shown at 514).

FIG. 8 therefore shows how palatouvuloplasty changed the frequency spectrum of breathing sounds from an up-shift pattern to a normal pattern. The spectrograms in FIG. 9 further indicated when specific frequency components occurred during the respiratory cycle. It is interesting to note that the frequency components corresponding to a specific peak in the frequency spectrum occurred either during inspiration or during expiration, but not both. This observation suggests the presence of temporary locality of breathing sounds and the different dynamics between inspiration and expiration.

Those skilled in the art will appreciate that the above described embodiments may be changed and modified without departing from the spirit and scope of the present invention.

What is claimed is:

1. A method of detecting obstructive sleep apnea in a subject, said method comprising the steps of:
    placing a head of an electronic stethoscope over the subject's suprasternal notch when said subject is in an awake state;
    providing an electrical signal representative of breathing sounds detected by the head of the electronic stethoscope within a frequency range, the breathing sounds corresponding to a patient breathing through their mouth;
    determining, by a processor, an obstructive sleep apnea index based on a ratio of an amount of energy of the electrical signal that is associated with a frequency below a cut-off frequency with respect to a total amount of energy associated with the entire frequency range, wherein the amount of energy associated with the frequency below the cut off frequency and the total amount of energy associated with the entire frequency range are each determined from a frequency spectrum of the electrical signal, wherein information regarding the frequency associated with the electrical signal are assessed in the frequency domain where frequency information from the frequency domain is used for calculating a spectral energy distribution of frequencies of the electrical signal to detect obstructive sleep apnea based on the spectral energy distribution of frequencies of the electrical signal; and
    identifying, by the processor, the subject as having obstructive sleep apnea if the obstructive sleep apnea index is above a window maximum or below a window minimum.

2. The method as claimed in claim 1, wherein said cut-off frequency is about 100 Hz.

3. The method as claimed in claim 1, wherein said frequency range is between about 20 Hz and about 800 Hz.

4. The method as claimed in claim 1, wherein said window maximum is about 80%.

5. The method as claimed in claim 1, wherein said window minimum is about 25%.

6. The method as claimed in claim 1, wherein said method further includes the step of identifying, by the processor, the subject as not having obstructive sleep apnea if the obstructive sleep apnea index is within a window defined between the window maximum and the window minimum.

7. A method of detecting obstructive sleep apnea in a subject, said method comprising the steps of:
    placing a head of an electronic stethoscope over the subject's suprasternal notch when said subject is in an awake state;
    providing an analog electrical signal representative of breathing sounds detected by the head of the electronic stethoscope within a frequency range, the breathing sounds corresponding to a patient breathing through their mouth;

receiving, by a recorder, the analog electrical signal and providing a digitized electrical signal to a processor that is representative of the analog electrical signal with the frequency range;

applying, by the processor, a fast Fourier transform to the digitized electrical signal;

determining, by the processor, an obstructive sleep apnea index based on a ratio of an amount of energy of the electrical signal that is associated with a frequency below a cut-off frequency with respect to a total amount of energy associated with the entire frequency range, wherein the amount of energy associated with the frequency below the cut off frequency and the total amount of energy associated with the entire frequency range are each determined from a frequency spectrum of the electrical signal, wherein information regarding the frequency associated with the electrical signal are assessed in the frequency domain where frequency information from the frequency domain is used for calculating a spectral energy distribution of frequencies of the electrical signal to detect obstructive sleep apnea based on the spectral energy distribution of frequencies of the electrical signal;

identifying, by the processor, the subject as having obstructive sleep apnea if the obstructive sleep apnea index is above a window maximum or below a window minimum; and identifying, by the processor, the subject as not having obstructive sleep apnea if the obstructive sleep apnea index is within a window defined by the window maximum and the window minimum.

8. The method as claimed in claim 7, wherein said cut-off frequency is about 100 Hz.

9. The method as claimed in claim 7, wherein said frequency range is between about 20 Hz and about 800 Hz.

10. The method as claimed in claim 7, wherein said window maximum is about 80%.

11. The method as claimed in claim 7, wherein said window minimum is about 25%.

12. A system for detecting obstructive sleep apnea in a subject, said system comprising:

an electronic stethoscope having a head for application to the subject;

an electrical signal representative of breathing sounds detected by the head of the electronic stethoscope within a frequency range below a cut-off, the breathing sounds corresponding to a patient breathing thru their mouth;

a processor for determining an obstructive sleep apnea index based on a ratio of an amount of energy of the electrical signal that is associated with the frequency below a cut-off frequency with respect to a total amount of energy associated with the entire frequency range, and for determining whether the obstructive sleep apnea index is above a window maximum or below a window minimum, wherein the amount of energy associated with the frequency below the cut off frequency and the total amount of energy associated with the entire frequency range are each determined from a frequency spectrum of the electrical signal, wherein information regarding the frequency associated with the electrical signal are assessed in the frequency domain where frequency information from the frequency domain is used for calculating a spectral energy distribution of frequencies of the electrical signal to detect obstructive sleep apnea based on the spectral energy distribution of frequencies of the electrical signal; and a display for providing an identification of whether the subject has obstructive sleep apnea responsive to whether the obstructive sleep apnea index is above the window maximum or below the window minimum.

13. The system as claimed in claim 12, wherein said processor and said display are provided within the electronic stethoscope.

* * * * *